United States Patent [19]

Linton

[11] Patent Number: 5,512,094

[45] Date of Patent: Apr. 30, 1996

[54] METAL OXIDE COATED SILICA SHELLS

[75] Inventor: Howard R. Linton, Nokomis, Fla.

[73] Assignee: E. I. Du Pont de Nemours and Company, Wilmington, Del.

[21] Appl. No.: 979,705

[22] Filed: Nov. 20, 1992

[51] Int. Cl.$^6$ .................................................. C08K 7/22
[52] U.S. Cl. ........................... 106/409; 106/456; 106/457
[58] Field of Search ..................................... 106/456, 457, 106/409

[56] References Cited

U.S. PATENT DOCUMENTS

| | | | |
|---|---|---|---|
| Re. 27,818 | 11/1973 | Werner | 106/437 |
| 2,885,366 | 5/1959 | Iler | 252/313 |
| 3,087,828 | 4/1963 | Linton | 106/417 |
| 4,199,614 | 4/1980 | Ziolo | 106/457 |
| 4,244,811 | 1/1981 | Grenoble et al. | 208/122 |
| 4,325,739 | 4/1982 | Biermann et al. | 106/403 |
| 4,349,372 | 9/1982 | Van Laethem et al. | 427/110 |
| 4,373,013 | 2/1983 | Yoshizumi | 428/570 |
| 4,431,764 | 2/1984 | Yoshizumi | 524/409 |
| 4,452,830 | 6/1984 | Yoshizumi | 427/215 |
| 4,473,621 | 9/1984 | Drylie | 428/576 |
| 4,621,024 | 11/1986 | Wright | 428/404 |
| 4,767,565 | 8/1988 | Demus et al. | 252/299 |
| 4,775,412 | 10/1988 | Nishikura et al. | 75/0.5 |
| 4,857,499 | 8/1989 | Ito et al. | 502/326 |
| 4,880,703 | 11/1989 | Sakamoto et al. | 428/378 |
| 4,917,952 | 4/1990 | Katamoto et al. | 428/403 |
| 4,944,985 | 7/1990 | Alexander et al. | 428/570 |
| 4,966,087 | 10/1990 | Child | 110/345 |
| 5,024,826 | 6/1991 | Linton | 423/335 |
| 5,041,162 | 8/1991 | Brand | 106/446 |
| 5,068,063 | 11/1991 | Tremper, III | 252/518 |
| 5,071,676 | 12/1991 | Jacobson | 427/214 |
| 5,104,583 | 4/1992 | Richardson | 252/518 |
| 5,114,756 | 5/1992 | Mirabeau et al. | 427/379 |
| 5,175,136 | 12/1992 | Felthouse | 502/242 |
| 5,178,736 | 1/1993 | Richardson | 204/181 |
| 5,236,737 | 8/1993 | Linton | 427/126.3 |
| 5,354,374 | 10/1994 | Prengel | 106/456 |

FOREIGN PATENT DOCUMENTS

| | | |
|---|---|---|
| 0267535 | 5/1988 | European Pat. Off. . |
| 0310340 | 4/1989 | European Pat. Off. . |
| 0359569 | 3/1990 | European Pat. Off. . |
| 3842330 | 6/1990 | Germany . |
| 59-86637 | 5/1984 | Japan . |
| 60-253112 | 12/1985 | Japan . |
| 61-63520 | 4/1986 | Japan . |
| 61-264345 | 11/1986 | Japan . |
| 62-18564 | 1/1987 | Japan . |
| 62-216105 | 9/1987 | Japan . |
| 63-20342 | 1/1988 | Japan . |
| 63-34180 | 2/1988 | Japan . |
| 63-200158 | 8/1988 | Japan . |
| 63-215745 | 9/1988 | Japan . |

OTHER PUBLICATIONS

"Inorganic and Theoretical Chemistry", J. W. Mellon, vol. I (1946), pp. 328–329, no month.
"Preparation And Properties Of Antimony–Doped $SnO_2$ Films By Thermal Decomposition Of Tin 2-ethylhexanoate", A. Tsunashima et al., pp. 2731–2735, Journal of Materials Science, v. 21, 1986, no month.
Japanese Patent Office Abstracts, JP–04–62713, Okuda et al., Feb. 1992.
Japanese Patent Office Abstracts, JP–01–111727, Katamoto et al. Apr. 1989.
Derwent Abstract C–88–157555; JP 63–265930, Nov. 1988.
Derwent Abstract 81–91986D/50; JP 56–140028, Nov. 1988.

Primary Examiner—Mark L. Bell
Assistant Examiner—Scott L. Hertzog
Attorney, Agent, or Firm—Michael K. Boyer

[57] ABSTRACT

The present invention discloses a novel high surface area powder composition in which the individual powder particles comprise hollow silica shells, e.g., amorphous hydroxylated silica, coated with finely distributed surface accessible metal oxides. The invention also discloses metallic coatings, which are obtained by converting at least a portion of the oxide coatings into the corresponding metals.

20 Claims, 1 Drawing Sheet

METAL OXIDE COATED SILICA SHELLS

FIELD OF THE INVENTION

The present invention relates to a novel high surface area powder composition in which the individual powder particles comprise silica shells, e.g., amorphous hydroxylated silica, coated with finely distributed surface accessible metal oxides.

BACKGROUND OF THE INVENTION

The production of silica shell structures is disclosed in U.S. Pat. No. 5,024,826, which issued on Jun. 18, 1991.

A process for coating silica shell structures with an antimony-containing tin oxide layer to produce electroconductive powders is described in European Patent Application Publication No. 0359569, which published on Mar. 21, 1990. Such electroconductive powders are useful in electrically conductive coatings, but generally not as primary conductors of electricity.

The entire content of U.S. Pat. No. 5,024,826, and European Patent Application Publication No. 0359569, is hereby incorporated by reference.

SUMMARY OF THE INVENTION

The present invention relates to a high surface area powder composition. The individual powder particles comprise about 0.05 to 15 micron silica shells, e.g., hollow amorphous hydroxylated silica shells, which have a shell thickness of from about 5 to 50 nm. The silica shells typically have a surface area of about 25 to 350 $m^2/g$.

At least a portion of the silica shell is coated with about 10 to 75% by eight of a finely distributed surface accessible metal containing species, e.g, a metal oxide. Surface accessible denotes that the metal oxide is situated on or about the outer surface of the silica shells. Suitable metal oxides comprise one or more members selected from the group of the oxides of Fe, Al, Zr, V, Nb, Ta, Cr, Mo, W, Co, Ni, Cu, Zn, Sn, Sb, mixtures thereof, among others.

One aspect of the invention relates to metallic coatings, which are obtained by converting or reducing at least a portion of the oxide coating to its corresponding metal. The metal oxide coating may be reduced by being exposed to an environment containing hydrogen or carbon monoxide at an elevated temperature, e.g., between about 550°–850° C. For example, a metal oxide coating comprising iron oxide can be reduced to iron at a temperature of about 550° C., whereas a nickel oxide coating can be reduced to nickel at a temperature of about 850° C.

The hollow shells can be prepared by any suitable process. One suitable process for preparing the shells is described in U.S. Pat. No. 5,024,826, which issued on Jun. 18, 1991, the teachings of which have been incorporated by reference.

A hydroxide of the metal containing species is deposited on the silica shells by adding, to an aqueous slurry of silica shells, a water soluble salt of the desired metal. An alkali metal hydroxide solution, e.g., sodium hydroxide solution, is added to the slurry in order to convert the salt to a metal hydroxide which deposits upon the silica shells. The hydroxide coated silica shells can be recovered from the aqueous slurry by any suitable means such as filtration, centrifugation, among other recovery techniques. The recovered shells can be washed with water until substantially free from soluble residues. At least a portion of the metal hydroxide coating can then converted to a metal oxide by thermally dehydrating the hydroxide coating.

Moreover, the metal oxide coating may be modified or reduced to tailor the characteristics of the powder to satisfy a particular end-use application. For example, a metal oxide coating comprising $Fe_2O_3$ may be converted to magnetic $Fe_3O_4$. In some cases, a metal oxide coating is reduced to obtain a metal coating by exposing the metal oxide to a reducing environment, e.g., hydrogen or carbon monoxide can be used to reduce iron oxide to Fe.

As a result of the hollow shell structure, the density of the metal or metal oxide coated powders of the invention is much lower than conventional solid or bulk powders. The low-density hollow-shell structure affords greater economy because the quantity of material necessary for a particular application is reduced in comparison to using either bulk metals or metal oxides. The economic advantages of the inventive powder are particularly useful in applications such as catalyst, toners, carriers for toners, pigments such as an automotive finish, electrical conductors, magnetic applications, transparent products, among many others.

When the powder coating upon the silica shell comprises, for example, $Fe_2O_3$, the powder is an effective ultra-violet (UV) ray absorber. Such a UV absorber is desirable for use in protective coatings, e.g., wood preservatives, color pigments, cosmetics, among many others.

DETAILED DESCRIPTION OF THE INVENTION

Figure 1:
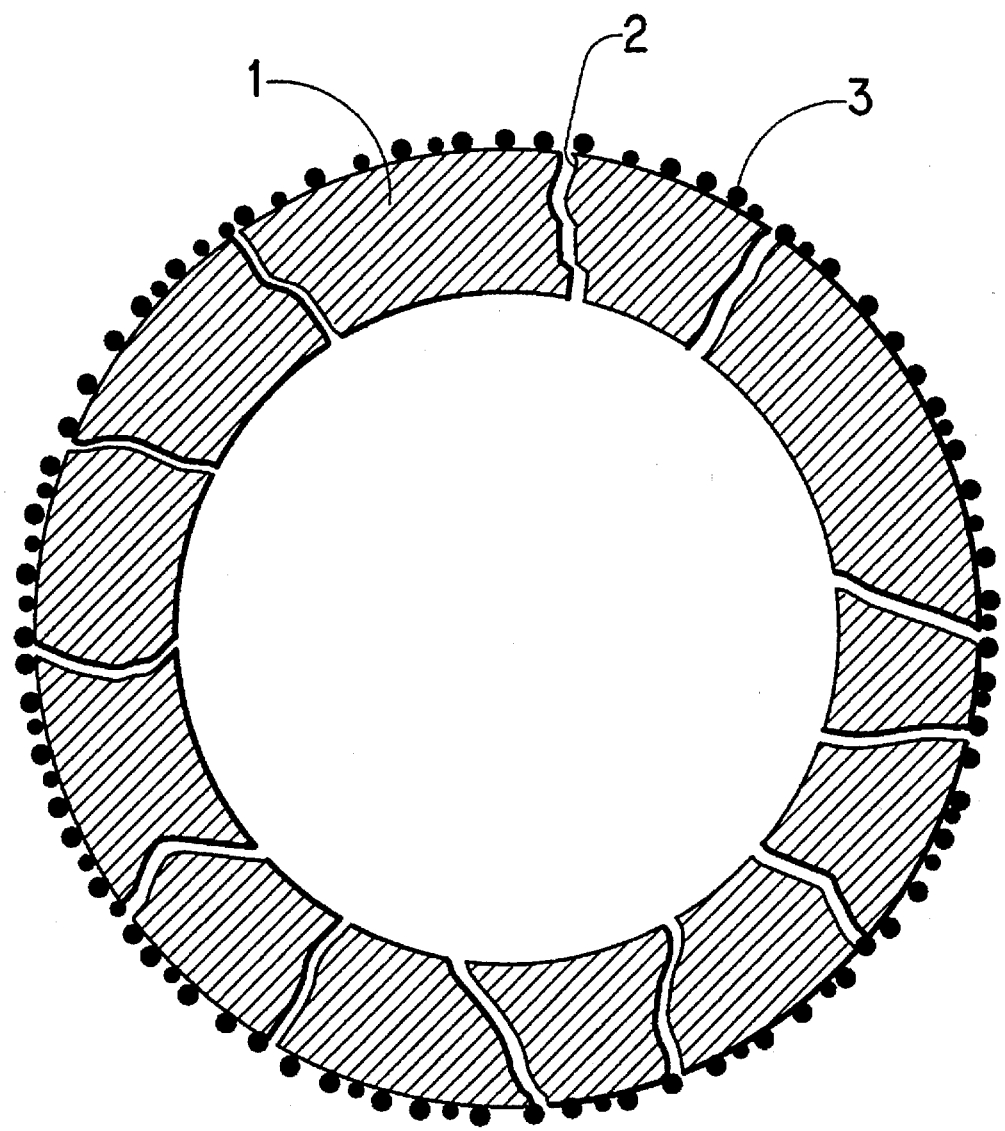
FIGURE 1 is a cross-sectional schematic drawing showing a hollow silica shell which has metal oxide particles deposited on the shell.

The present invention relates to a high surface area powder composition, and to a method for producing the powder. The individual powder particles comprise about 0.05 to 15 micron silica shells, e.g., amorphous hydroxylated silica, which have a shell thickness of from about 5 to 50 nm, and a surface area of from about 25 to 350 $m^2/g$. The silica shells are coated with about 10 to 75% by weight of a finely distributed surface accessible metal containing species, e.g., a metal oxide.

Whenever used in the specification and appended claims the terms below are intended to have the following definitions.

"Finely distributed" as used herein refers to the characteristics of the metal containing species. Typically, metal containing species comprise crystallites which have an average size of about 50 to 200 Angstroms. The metal containing species may not completely surround the silica shell, but rather in some cases form an at least partially interconnected network about the silica shell. For example, the density or loading of metal containing species may range from trace amounts to a substantially complete coating or monolayer.

"Metal containing species" as used herein refers to the composition and morphology of the metal and/or metal oxide which is present upon at least a portion of the silica shell. The metal and/or metal oxide containing species may include one or more compositions in a variety of morphologies. Typically, the morphology of the metal and/or metal oxide is crystalline. However, the presence of amorphous material is permissible, and may be desirable when the coated powder is employed as a catalyst.

"Surface accessible" denotes that the metal containing species are situated on or about the outer surface of the silica shells. This term does not include species which are incorporated within the silica shell structure. Suitable metals and oxides thereof comprise at least one member selected from the group of Fe, Al, Zr, V, Nb, Ta, Cr, Mo, W, Co, Ni, Cu, Zn, Sn, Sb, mixtures thereof, among others.

"Silica shell" as used herein refers to the characteristics and composition of the shell upon which the metal containing species are deposited. The silica shell is normally hollow, and can be employed in a wide range of sizes, shapes, and shell thicknesses. In some cases, the core material is not removed, and the silica shell is characterized by a skin which surrounds the core material. In such cases, the silica shell or skin may also include additional components such as alumina, boric oxide, among others. The additional components as well as the core material can be removed by acid extraction.

Suitable hollow shells, which will support the metal containing species, can be prepared by the procedures described in U.S. Pat. No. 5,024,826 which issued on Jun. 18, 1991; the teachings of which have been incorporated herein by reference. The metal containing species can be deposited on the silica shells by forming an aqueous slurry comprising previously formed silica shells, soluble salts of the desired metal containing species, and an alkali hydroxide.

The average size and shape of the powder particles is controlled by the configuration of the silica shells. By appropriately selecting the silica shells upon which the metal containing species are to be deposited, the invention can tailor the physical characteristics of the powder. The silica shells may be 1) equiaxial particles which have an average diameter of from about 0.05 to 15 microns, 2) acicular particles that have an aspect ratio of from about 2 to 50, and an average diameter of from 0.1 to 0.5 microns, and; 3) platelike particles which have an aspect ratio of from 10 to 150, and an average diameter of 2 to 15 microns, among others. The surface area of the silica shells typically ranges from about 25 to 350 $m^2/g$, and the shell thickness is from about 5 to 50 nm; usually from about 10 to 20 nm.

A hydroxide of the metal containing species can be deposited on the silica shells by adding, to an aqueous slurry of silica shells, at least one soluble salt of the desired metal oxide, and an alkali metal hydroxide solution. The silica shells, which are at least partially coated with a metal hydroxide, can be recovered from the aqueous slurry by filtration, centrifugation, vacuum filtration, among others, and washed with water until substantially free from soluble residues. At least a portion of the metal hydroxide upon the silica shells is then converted into a metal oxide by thermally dehydrating the hydroxide. The metal oxide coating may then be reduced further to obtain a coating of a reduced oxide and/or the corresponding metal. In this aspect of the invention, the metal oxide is reduced, for example, to a metal by being exposed to a high-temperature reducing environment, e.g., hydrogen or carbon monoxide.

The metal oxide is typically present as finely distributed sub-micron size crystallites, which are deposited on or about at least a portion of the outer surface of the silica shells, e.g., refer to FIGURE 1 which is discussed below in greater detail. The average size of the metal oxide crystallites ranges from about 50 to 200 Angstroms. The amount of metal oxide which is present can range from about 10 to 75% by weight of the powder composition. The particular amount of metal containing species, e.g., metal oxide, which is provided upon the surface of the silica shell, will depend upon the intended end-use of the coated powder. For example, when employing a metal oxide as catalyst a relatively small amount of metal oxide is typically present upon the silica shell, whereas an ultraviolet light absorbing metal oxide may require a relatively large amount. In some cases, at least a portion of the finely distributed metal species are located within the pores of the silica shell, i.e., the pores which were formed during acid extraction to remove the core material.

The physical characteristics of the coated powder can be better understood by reference to FIGURE 1, which is a cross-sectional schematic drawing that shows a coated hollow silica shell. Referring now to FIGURE 1, 1 refers to a representative silica shell which has pores 2. Such pores typically result when the core material (not shown) is removed. A metal oxide and/or metal crystallites 3 are present generally on or about the outer surface of silica shell 1. In some cases, crystallites 3 are present within pore 2.

For certain end-use applications, a silica shell coating can comprising oxides such as FeOOH, alpha $Fe_2O_3$, among others. Such iron oxide coated shells are also useful as precursors for shell products which are coated further and/or converted to materials such as with $Fe_3O_4$, gamma $Fe_2O_3$, Fe metal, among others. The precursor can be converted or reduced by being heated in a reducing environment, e.g., containing hydrogen, carbon monoxide, among others. These iron and iron oxide coated shells possess desirable dispersion characteristics, and low densities when compared with conventional iron oxide powders. Iron oxide coated powders of the invention are useful as toners, brown pigments for an automotive finish, among others. When the iron oxide coating is converted into $Fe_3O_4$, the resultant magnetic properties of the coated silica shells enable the shells to be used in a variety of electronic applications, e.g, circuit boards, carrier for toner, among others.

The size and shape of the coated powders can be controlled, e.g., by appropriately selecting a core material which is used to form the silica shell, to obtain a wide range of products, e.g., transparent coatings, films, among others. The thickness of the metal or metal oxide coating upon the silica shells can be varied by controlling the composition of the hydroxide reducing agent, process temperatures, reaction time, among others. Thus, the composition, configuration, size, among others, of the powder can be tailored to satisfy a wide range of end-use applications.

In another aspect of the invention, at least a portion of the silica shells can be coated with an intermediate material before depositing the metal containing species. For example, an intermediate coating which comprises one or more members from the group of alumina, tin oxide, zirconium oxide, among others, can be deposited upon the silica shell. The intermediate coating can be applied by any suitable technique such as hydrolysis of a soluble salt. When employing an intermediate coating, it is normally expedient to deposit the coating using salt hydrolysis techniques which are similar to those used to deposit the metal containing species. In some cases, it may be desirable to deposit a plurality of layers upon the silica shell before, during, and/or after depositing the metal containing species. Such layers can be either chemically similar and/or distinct.

Yet another aspect of the invention relates to forming metallic coatings upon the silica shells, which are obtained by converting at least a portion of the oxide coatings to its corresponding metal, e.g., converting iron oxide to iron. The metallic coatings can be formed by exposing the metal oxide to a high-temperature reducing environment, e.g., gaseous hydrogen, carbon monoxide, among others. For example, a metal oxide coating upon a silica shell can be reduced to a metal be being heated to a temperature of about 500°–900° C., and contacted with an atmosphere comprising at least one member of hydrogen, carbon monoxide, among others.

A powder composition of the invention can be prepared by a process which generally comprises:

(a) coating an aqueous slurry of a finely divided inert core material such as calcium and/or barium carbonate, among others, with silica, e.g., amorphous hydroxylated silica;

(b) removing the core material, e.g., by acid extraction, thereby obtaining an aqueous slurry of hollow shells;

(c) recovering the silica shells, washing the shells substantially free from soluble residues or species, and optionally drying;

(d) preparing an aqueous slurry of the silica shells, and depositing at least one finely distributed metal hydroxide upon the shell, which is obtained by adding to the aqueous shell slurry at least one soluble salt of the desired metal, and an alkali metal hydroxide;

(e) recovering the solids, washing the solids substantially free from water soluble residues or species and drying;

(f) heating the solids to convert the coating of hydroxide to oxide; and (g) optionally heating the oxide coated particles in a reducing atmosphere to convert the oxide coating to a reduced oxide and/or the corresponding metal.

In one aspect of the invention, the core material is not removed, and a silica skin is coated with a finely distributed metal containing species. Should the presence of the core material be desired, the pH, which is used in further processing, should be controlled in order to prevent dissolution of the core. In this aspect of the invention, the silica shell and/or skin composition can be modified to include additional components. Examples of suitable additional components comprise one or more members from the group of boric oxide, aluminum oxide, zirconium oxide, among others. For example, when employing a process which deposits silica upon a core material, one or more salts of an additional skin component can be deposited along with the silica. The additional component, which may be present as a complex oxide, mixture or solid solution with silica, becomes a part of the skin. If desired, at least a portion of the additional component and the core material can be removed by exposing such a skin to an appropriate acid. Whether or not the additional component is removed, by employing an effective quantity of an additional component when depositing silica upon the core material., the surface area of the resultant powder can be increased.

The silica shells can be coated by preparing a suspension, which contains about 100 to 700 g/l of silica shells, that is heated to about 40° C. and 90° C., and typically continuously agitated. Any suitable means, such as a paddle stirrer, can be employed to agitate the suspension. An aqueous solution of at least one metal salt, e.g, an aqueous solution of a mixture of metal salts, and an aqueous alkali metal hydroxide, e.g., ammonium hydroxide solution, sodium hydroxide, among others, are typically added concurrently to the agitated slurry while maintaining the pH between about 2 and 8. After adding all the reagents to the slurry, agitating and heating are usually continued for about half an hour to one hour for ensuring substantially complete deposition of the metal hydroxide upon the silica shells.

Any suitable water soluble salts can be employed as the source of the metal containing species or oxides. Suitable water soluble salts include chlorides, nitrates, among others. The concentration of the salt solutions typically ranges from about 50 g/l to 600 g/l, when the desired metal containing species of the product is between 10 to 75 wt %. When the desired quantity of metal containing species is greater, the concentration of the salt can be increased.

During the deposition of the metal hydroxides, the pH of the suspension can be controlled. Typically, the pH will be decreased by adding an acid such as HCl. However, when the pH becomes too great a basic material such as NaOH is added to the suspension. By introducing the appropriate quantity of acid and/or basic material, the pH can be controlled to satisfy a desired range.

The solids, which comprise metal hydroxide coated silica shells, can be recovered from the slurry by any suitable process such as filtration, centrifugation, vacuum filtration, among others. The recovered solids can be washed with water until substantially free from soluble residues, and normally dried at a temperature which ranges from about 110° to 150° C.

The dry solids can be calcined in an oxidizing atmosphere, for example, air at a temperature which ranges from about 550° to 900° C., and normally about 750° C. Typically, the powder is calcined for about one to two hours, in order to convert at least a portion of the deposited hydroxides to the corresponding oxides.

At least a portion of the oxide coating on the silica shells may be reduced to a lower oxide and/or to the corresponding metal. The oxide coating is reduced by being heated in a reducing atmosphere, such as hydrogen, carbon monoxide, among others, at a temperature which ranges from about 300 to 800° C.

While particular emphasis in the above description has been placed upon silica shells which are coated with a metal containing species such as a metal and oxides thereof, the invention is capable of producing a wide range of products. For example, the composition of the silica skin, which surrounds a core material, may be modified, for example, to include other materials such as $B_2O_3$, $Al_2O_3$, $ZrO_2$, among others. Further, one or more metal containing species may be deposited upon the silica shells either simultaneously and/or as sequential layers. Accordingly, the present invention can be employed to produce a product which has been tailored to satisfy a wide range of end-use applications.

Compositions of the invention and processes for obtaining the same are illustrated in greater detail by the following Examples which are not to be construed as limiting in any way the scope of the invention. Unless specified otherwise, percentages are in weight percent, and the materials used in these Examples were commercially available.

EXAMPLE 1

This Example describes a process for preparing iron oxide coated silica shells.

About three liters of de-ionized water was added to a 1-gallon Waring blender jar, and the pH was increased to about 10.0 by adding 20% NaOH. A stock solution which comprised potassium silicate was produced that had a $SiO_2$/$K_2O$ molar ratio of about 3.3, and contained about 26 wt % $SiO_2$. Approximately 100 g of this stock solution was added to the solution in the Waring Blender jar and thereafter about 1,700 g of $CaCO_3$ powder, (Albacor H.O. Dry, available from Pfizer Corp.) was added to form a mixture. The mixture was blended at high speed for about two minutes to form a slurry.

The slurry was transferred to a 18-liter, polyethylene beaker, steam heated to about 90° C., stirred for about one half-hour (the pH was about 9.5). Next about 1,027 g of the potassium silicate stock solution, described above, was diluted with water to 1 liter, and added to the slurry over a period of about 4 hours. The pH was maintained at about 9.0 by the concurrent addition of hydrochloric acid. The hydrochloric acid used for controlling the pH consisted of about 255 ml 37% HCl diluted with water to 1 liter.

The slurry, which had a pH of about 9.0, and a temperature of about 90° C., was stirred for about one half-hour. The pH was decreased to about 7.5 by adding hydrochloric acid, which caused solids to flocculate. The solids were washed with de-ionized water to remove soluble species, and dried in an air oven at about 110° C. The dry powder weighed about 1931 g, and had a nitrogen surface area of about 7.8 $m^2/g$.

Approximately 500 ml of deionized water, and 300 g of the dry solids were admixed in a Waring Blender for two minutes to form a slurry. The slurry was transferred to a polyethylene beaker which was agitated. After diluting the slurry with water to 1 liter, and heating to 90° C. with steam, approximately 415 ml of 37% HCl was added to reduce the pH to 2.0, which removed the $CaCO_3$ cores and formed substantially hollow silica shells.

A solution was prepared containing about 85 g $FeCl_3.5H_2O$, (equivalent to 27 g $Fe_2O_3$), within about 200 ml of water. This solution was added to the aqueous slurry of silica shells concurrently with 20% NaOH over a period of about two hours, at a temperature of about 90° C., while maintaining the pH at about 2.5. The slurry was stirred, and the resultant solids separated by filtration. The solids were washed with de-ionized water to remove soluble species and dried in an air oven at about 110° C. Approximately 73 g of a light brown to yellow powder were recovered. When this powder was heated in a hydrogen environment at 550° C. for about two hours, a black magnetic powder was obtained.

EXAMPLE 2

This Example describes a process for preparing aluminum oxide coated silica shells.

A procedure substantially in accordance with Example 1 was used to obtain a dilute aqueous solution of potassium silicate. To this solution was added 600 g of $CaCO_3$ powder, (Albacor H. O. Dry, available from Pfizer Corp.), while mixed in a 1-gallon high speed Waring blender jar for about two minutes which formed a slurry. The slurry was transferred to a 18-liter polyethylene beaker, steam heated to about 90° C. in one half-hour, stirred (after which the pH was 9.8). Next about 1,027 g of a potassium silicate stock solution, which had a $SiO_2/K_2O$ molar ratio of 3.3, and contained about 26 wt % $SiO_2$, was diluted with water to 1 liter. The diluted potassium silicate was added to the slurry over a period of about 4 hours.

The pH of the slurry was maintained at about 8.5 by the concurrent addition of a solution which comprised about 209 ml 37% HCl, 28 g $CaCl_2.2H_2O$, and 1 liter of water. The slurry was then stirred at 90° C. and pH 8.5 for 15 minutes. The pH of the slurry was adjusted to about 7.0 by adding HCl. The slurry was allowed to stand undisturbed overnight to permit the solids to settle. The solids were separated by decantation, and washed several times by slurrying with deionized water and decanting.

The washed and decanted solids were re-slurried with one liter of 37% HCl, which changed the pH to about 2.0, and heated to about 90° C., thereby removing the $CaCO_3$ cores and forming hollow silica shells. The pH of silica shell slurry was adjusted to about 4.5 by adding 20% NaOH. About one liter of an aqueous solution containing approximately 110 g of $Al(NO_3)_3.9H_2O$ was added, and stirred into the slurry. The pH was maintained at about 4.5 by adding 20% NaOH, and the temperature at 90° C. The slurry was then stirred while at a temperature of about 90° C., a pH of about 4.5, for one half-hour after which produced solids. The solids were recovered substantially in accordance with the procedures described in Example 1.

EXAMPLE 3

This Example describes a process for preparing zirconium oxide coated silica shells.

A slurry comprising about 200 g $CaCO_3$ powder (Albacor H.O. Dry available from Pfizer Corp.), and about 2500 ml of de-ionized water was prepared in a 4 liter beaker. The slurry was agitated, heated to about 80° C., and the pH adjusted to 9.5 by adding 20% NaOH. A solution comprising potassium silicate was prepared by diluting about 200 g of the potassium silicate stock solution described in Example 2 into about 200 ml of a solution comprising de-ionized water and calcium chloride. (The solution containing calcium chloride was prepared by dissolving about 50 g of $CaCl_2$ into 1 liter of de-ionized water). All the potassium silicate solution and about 10 ml of the $CaCl_2$ solution were added concurrently to the agitated $CaCO_3$ slurry over a period of about 2 hours, at a temperature of about 80° C., while maintaining the pH at 9.5 by adding 20% HCl. The resultant slurry was then stirred, while at a temperature of about 80° C. and a pH of about 9.5, for 30 minutes.

The pH of the agitated slurry was decreased to about 2.0 by adding 340 ml 37% HCl, removing the $CaCO_3$ cores and form silica shells. Approximately 1230 ml of a solution comprising $ZrOCl_2$, which contained the equivalent of 20 wt % $ZrO_2$, was then added to the slurry of silica shells over a two hour period, while maintaining the pH at about 2.0 by adding 20% NaOH. The slurry was stirred for about 30 minutes after which the solids were separated by filtration. The solids were washed with de-ionized water to remove soluble species and dried in an air oven at about 120° C. About 487g of powder was recovered.

The nitrogen surface area of the recovered powder was about 189 $m^2/g$. Two samples of the recovered powder were calcined, respectively, at 1000° C. and 1200° C., for about one hour. The calcined powders were analyzed by x-ray diffraction, and found to contain a major phase corresponding to tetragonal $ZrO_2$ and a minor phase of monoclinic $ZrO_2$.

EXAMPLE 4

This Example describes a process for preparing silica shells coated with chromium and antimony oxides.

A $CaCO_3$ slurry substantially as that described in Example 3 was prepared in a 2-liter beaker using about 100 g of $CaCO_3$ and 1000 ml of de-ionized water. The slurry was agitated, heated to 90° C., and the pH adjusted to about 9.5 by adding 20% NaOH. A solution of potassium silicate was prepared by diluting about 100 g of the potassium silicate stock solution, described in Example 2, to 200 ml with deionized water. The diluted stock solution was added to the agitated $CaCO_3$ slurry over a period of about 2 hours, at 90° C., while maintaining the pH at about 9.5 by adding 20% HCl. The slurry was stirred for about 30 minutes.

The pH of the agitated slurry was decreased to about 2.0 by adding about 170 ml of 37% HCl, thereby removing the $CaCO_3$ cores and forming hollow silica shells. A solution comprising chromium chloride was prepared by dissolving about 27 g of $CrCl_3.6H_2O$ into 100 ml of 37% HCl. A solution comprising antimony chloride was prepared by dissolving about 500 g $SbCl_3$ into 1000 ml of 37% HCl. Then, approximately 48 ml of the antimony chloride solution was admixed with the chromium chloride solution, and the mixture was added to the silica shell slurry over an about one hour period. The pH was maintained at about 2.0 by adding 20% NaOH. The slurry was stirred for about 30 minutes after which the solids were filtered, washed and dried substantially as described in Example 3. About 46 g of powder was recovered.

The nitrogen surface area of the recovered powder was about 142 $m^2/g$. A sample of the powder was taken and calcined at about 500° C. The calcined powder was analyzed by x-ray diffraction which indicated that the powder contained a major crystalline phase which corresponded to $CrSbO_4$. Further analysis by EDAX showed Si, Cr and Sb to be the only metallic elements present in the calcined powder.

EXAMPLE 5

This Example describes a process for preparing silica shells coated with iron, nickel and zinc oxides.

A $CaCO_3$ slurry was prepared substantially in accordance with Example 4, by using about 1200 ml of de-ionized water. Two solutions which, respectively, comprised potassium silicate and calcium chloride were prepared substantially in accordance with Example 3, by using about 100 g the potassium silicate stock solution described above. All the potassium silicate solution, which was prepared, and about 10 ml of the $CaCl_2$ were added concurrently to an agitated $CaCO_3$ slurry over a period of 2 hours. The temperature of the slurry was about 80° C. The pH was maintained at about 9.5 by adding 20% HCl. The slurry was stirred for about 30 minutes.

The pH of the agitated slurry was then decreased to about 2.0 by adding about 170 ml of 37% HCl, which removed the $CaCO_3$ cores, thereby forming silica shells.

A solution comprising iron chloride was prepared by dissolving about 100 g of $FeCl_3.6H_2O$ into 250 ml of 7.5% HCl. The iron chloride solution was added to the agitated silica shell slurry, which was at 80° C., over an approximately 2 hour period, while maintaining the pH at about 2.0 by adding 20% NaOH. The slurry was stirred for about 30 minutes, after which the solids were separated by filtration. The solids were washed several times with de-ionized water to remove soluble species, which produced a filter cake.

The washed filter cake was re-slurried in about 500 ml of de-ionized water within a 2 liter beaker, and heated to about 60° C. A solution comprising nickel chloride was prepared by dissolving about 22 g of $NiCl_2.6H_2O$ into 50 ml of de-ionized water. Another solution which comprised zinc chloride was prepared by dissolving about 13 g of zinc chloride into 50 ml of de-ionized water. These two solutions were admixed together, and about two ml of 37% HCl was added. The solution mixture was added to the filter cake slurry over a period of about one hour, at a temperature of 60° C., while maintaining the pH at about 8.5 by adding 20% NaOH. The resultant slurry was stirred for about 30 minutes after which the solids were separated by filtration, washed, and dried substantially in the manner described in Example 3. About 80 g of powder was recovered.

A portion of the recovered powder was calcined in air for about 1 hour at a temperature of about 900° C. The calcined sample was examined by X-ray diffraction analysis which indicated the presence of a phase that corresponded to magnetite, i.e., $Fe_3O_4$.

EXAMPLE 6

This Example describes a process for preparing silica shells which are coated with iron, tin and antimony oxides.

An aqueous slurry of silica shell particles was prepared substantially in the manner described in Example 5, with the exception that about 100 g of potassium silicate stock solution was diluted to about 100 ml with de-ionized water, and about 5 ml of $CaCl_2$ solution, (50 g/l) was used.

A solution comprising iron chloride was added to an agitated slurry of silica shells, which had a temperature of about 80° C., over an approximately two hour period substantially in the manner described in Example 5.

A solution comprising about 140 ml of a 37% HCl solution which contained $SnCl_4$, (equivalent to 0.375 g $SnO_2$/ml), and $SbCl_3$, (equivalent to 0.100 g $Sb_2O_3$/ml), was added to the agitated slurry. The solution was added over an approximately 2 hour period while maintaining the pH at 2.0 by adding 20% NaOH. The slurry was stirred for about 30 minutes, after which the solids were separated by filtration, washed, and dried substantially in the manner described in Example 3. About 123 g of powder was recovered.

A portion of the powder was calcined in air at about 750° C. for a period of about 2 hours. A sample of the calcined powder was examined by X-ray diffraction analysis which indicated the presence of a major crystalline phase that corresponded to $SnO_2$ with a trace of crystalline $Fe_2O_3$.

EXAMPLE 7

This Example describes a process for preparing iron coated silica shells.

Approximately 100 g of $CaCO_3$ powder was slurried into a 1 liter of de-ionized water within a stirred 2 liter beaker. The slurry was heated to about 90° C., and the pH was increased to about 9.5 by adding 20% NaOH.

About 100 g of potassium silicate stock solution substantially as described in Example 1 was diluted to 200 ml with de-ionized water. About 50 g of $CaCl_2$ was dissolved into 1 liter of de-ionized water. Approximately 200 ml of diluted $K_2SiO_3$, and 10 ml of $CaCl_2$ solution were added concurrently to the $CaCO_3$ slurry, which was at a temperature of about 90° C., and continuously agitated for about 2 hours while maintaining the pH at about 9.5 by adding 20% HCl. The slurry was stirred for an additional 30 minutes.

About 172 ml of concentrated HCl was then added to the slurry for decreasing the pH of the slurry to about 2.0, which removed the $CaCO_3$ cores, thereby forming hollow silica shells.

A solution was prepared which contained about 114 g of $FeCl_3.6H_2O$, (equivalent to 67.38 g of $Fe_2O_3$), in 100 ml of water, and about 100 ml concentrated HCl. This solution was added to the aqueous slurry concurrently with 20% NaOH over a period of 90 minutes while maintaining the temperature at about 90° C., and the pH at 2.0. The slurry was stirred for a further 30 minutes, and the solids separated by filtration. The separated solids were washed with de-ionized water to remove soluble species, and dried in an air oven at about 120° C. Approximately 65 g of powder was recovered.

The recovered powder was calcined in air at about 600° C. for about 2 hours. A sample of the calcined powder was taken. The nitrogen surface area of the calcined powder was about 117 $m^2/g$. The calcined powder was examined by X-ray diffraction analysis which indicated the presence of amorphous material that gave a weak broad peak pattern corresponding to FeOOH.

Approximately 4 g of the calcined powder was placed in an alumina boat and loaded into a horizontal tube furnace. The powder was heated at about 750° C. for about 90 minutes within a reducing atmosphere which contained 50% hydrogen. After cooling the furnace to room temperature the reduced powder was examined by x-ray diffraction analysis, which indicated that the powder contained $Fe_2SiO_4$ and Fe as the major crystalline phases. The iron content as determined by EDAX analysis was about 60%. The average crystallite size of the iron was about 1130 Angstroms.

EXAMPLE 8

This Example describes a process for preparing nickel coated silica shells.

Substantially in accordance with the procedure described in Example 1, about 100 g of $CaCO_3$ powder was slurried into one liter of de-ionized water. The slurry was heated to about 80° C., and the pH was increased to about 9.5 by adding 20% NaOH.

Approximately 100 g of the stock $K_2SiO_3$ solution, described in Example 1, was diluted to 200 ml by using de-ionized water. About 50 g of $CaCl_2$ was dissolved in one liter of de-ionized water. The diluted $K_2SiO_3$ solution and 10 ml of the $CaCl_2$ solution were added concurrently over a period of two hours to the $CaCO_3$ slurry. The temperature of the slurry was maintained at about 80° C., and the pH at about 9.5 by adding 20% HCl. The slurry was stirred for about half hour.

About 175 ml of concentrated HCl was slowly added to the slurry, and the pH was stabilized at about 2.0. Next the pH of the slurry was increased to about 8.0 by adding 20% NaOH. A solution comprising 120 g of nickel chloride, $NiCl_2 \cdot 6H_2O$, about 100 ml concentrated HCl, and 100 ml of de-ionized water, was added to the agitated slurry over a two hour period during which the pH was kept at about 8.0 by adding 20% NaOH.

After a period, the solids from the slurry were recovered by filtration, washed, and dried in an air oven at 120° C. The dry powder yield was about 77g, and the nitrogen surface area of the product was about 377 $m^2/g$.

The dried powder was charged into two 10"×1" alumina boats, and loaded into a horizontal tube furnace. The powder was heated to about 800° C. for about 3 hours in an atmosphere consisting of about 50% hydrogen and 50% argon. After cooling the powder to room temperature, tinder argon a black powder was obtained. The black powder was examined by X-ray diffraction analysis which indicated that nickel was the major crystalline phase with a minor amount of NiO.

EXAMPLE 9

This Example describes a process for preparing copper coated silica shells which have an intermediate titania coating.

A procedure substantially in accordance with Example 6 was used to obtain an aqueous agitated slurry of silica shells. Approximately 30 ml of a solution of $SnCl_4$, (equivalent to 0.445 g of $SnO_2$/ml), was added to the slurry which was at a temperature of about 80° C., over a period of about 20 minutes.

Next a solution comprising about 100 ml of $TiCl_4$ (28.2%), 2.5 ml of $SnCl_4$ solution, and 25 ml of concentrated HCl was added over a period of 1½ hours to the agitated slurry, while maintaining the temperature at about 80° C. and the pH at about 2.0 by adding 20% NaOH. After about half an hour the solids from the slurry were recovered by filtration, washed, and dried in an air oven at about 120° C. The dry product yield of $TiO_2$ coated silica shell particles was about 58 g.

Approximately 40 g of the above product was slurried into about 350 ml of de-ionized water. About 2 g of copper acetate, $[Cu(CH_3 \cdot COO)_2]$, was added to this slurry, and the pH was adjusted to about 8.0 with 20% NaOH. A solution of copper acetate, which comprised about 20 g of $Cu(CH_3 \cdot COO)_2$ dissolved into 100 ml of de-ionized water, was added to the slurry over a period of about one hour. The slurry was stirred for about 30 minutes.

The solids were recovered from the slurry by filtration, washed substantially free from soluble species, dried at about 120° C., and calcined at about 800° C. for two hours. The dry product yield was about 44 g. The product was examined by X-ray diffraction analysis which indicated that the major crystalline phases corresponded to $SnO_2$, $TiO_2$ and CuO. The X-ray pattern also indicated the presence of some amorphous material.

A portion of the calcined powder was reduced by being exposed to a high temperature hydrogen-containing environment substantially in the manner described in Example 5. The reduction conditions were 600° C. for two hours. The calcined powder was examined by X-ray diffraction analysis which indicated that the major crystalline phase corresponded to Cu, a minor phase of $TiO_2$, and trace amounts of CuO and $SnO_2$. The X-ray pattern also indicated the presence of some amorphous material.

While certain desirable aspects of the invention have been described above in detail, a person in this art will recognize that a variety of variations and embodiments are encompassed by the appended claims.

The following is claimed:

1. A powder composition in which the powder particles comprise a hollow silica shell that has an average diameter in the range of about 0.05 to 15 microns, a shell thickness in the range of from about 5 to 50 nanometers, and surface area of about 25 to 350 $m^2/g$, said silica shell having a surface accessible coating comprising at least one metal oxide selected from the group consisting of Fe, Zr, V, Nb, Ta, Cr, Mo, W, Co, Ni, Cu, and Zn, wherein said at least one metal oxide comprises about 10 to 75% by weight of the powder composition.

2. A process for preparing a powder composition, the process comprising the steps of:

(a) applying to a slurry comprising finely divided core particles, a coating comprising silica, (b) optionally dissolving the core material to form an aqueous slurry comprising hollow shell shells, (c) recovering the shells, washing said shells substantially free from soluble residues, and optionally drying, (d) preparing an aqueous slurry comprising the silica shells, and depositing at least one finely distributed metal hydroxide upon said shells, by adding to the aqueous slurry at least one water soluble salt of said metal hydroxide, and an alkali metal hydroxide, (e) recovering the solids from the slurry thereby obtaining silica shells which are at least partially coated with a metal hydroxide, and;

(f) heating the recovered shells to convert at least a portion of said metal hydroxide coating to a surface accessible metal oxide, wherein said metal oxide comprises at least one oxide of the metals selected from the group of Fe, Zr, V, Nb, Ta, Cr, Mo, W, Co, Ni, Cu and Zn.

3. A process for preparing a ultra-violet light absorbing powder, the process comprising the steps of:

(a) preparing an aqueous slurry comprising hollow silica shells, (b) applying a coating of at least one ultra-violet light absorbing material upon at least a portion of said shells, by adding at least one water soluble salt which corresponds to said material, and an alkali hydroxide, (c) recovering the solids from the slurry thereby obtaining silica shells which are at least partially coated a hydroxide of said absorbing material, and;

(d) heating the recovered shell to convert at least a portion of said hydroxide to a surface accessible metal oxide.

4. The process of claim 2 or 3, further comprising convening at least a portion of said oxide into a metal by being exposed to a reducing atmosphere.

5. The composition of claim 1, wherein at least a portion of said coating comprises a metal.

6. The process of claim 3 wherein said metal oxide comprises at least one oxide or the metals selected from the group of Fe, Zr, V, Nb, Ta, Cr, Mo, W, Co, Ni, Cu and Zn.

7. The process of claim 3, wherein said absorbing material comprises iron oxide.

8. The process of claim 2, 3, or 5 wherein said metal oxide comprises $Fe_2O_3$ wherein at least a portion of said $Fe_2O_3$ is convened to $Fe_3O_4$.

9. The composition of claim 1, wherein said powder comprises at least one member of the group consisting of a pigment, toner, catalyst and an ultra-violet absorbing material.

10. The process of claim 2 or 3, wherein the amount said metal oxide ranges from about 10 to 75% by weight.

11. The composition of claim 1 wherein said surface accessible coating comprises crystallites which have an average size of about 50 to 200 angstroms.

12. The composition of claim 1 further comprising an intermediate coating comprising at least one member selected from the group consisting of alumina, tin oxide, titanium oxide and zirconium oxide which is located between the hollow silica shell and surface accessible coating.

13. The process of claim 2 or 3 further comprising depositing an intermediate coating comprising at least one member selected from the group consisting of alumina, titanium dioxide, tin oxide and zirconium oxide upon the silica shells.

14. The composition of claim 1 or 12 wherein the surface accessible coating comprises oxides of chrome and iron.

15. The composition of claim 1 or 12 wherein the surface accessible coating comprises oxides of iron, nickel and zinc.

16. The composition of claim 1 or 12 wherein the surface accessible coating comprises oxides of iron, tin and antimony.

17. The composition of claim 3 or 12 wherein the surface accessible coating comprises copper and the intermediate coating comprises titanium dioxide.

18. The process of claim 2 or 3 wherein the silica shell further comprises at least one member selected from the group consisting of boric oxide, aluminum oxide and zirconium oxide.

19. The process of claim 2 or 3 wherein the water soluble salt comprises a chloride or nitrate.

20. The composition of claim 1 wherein the silica shell further comprises at least one member selected from the group consisting of boric oxide, aluminum oxide and zirconium oxide.

* * * * *